(12) United States Patent
Milla et al.

(10) Patent No.: US 7,176,318 B2
(45) Date of Patent: Feb. 13, 2007

(54) PROCESSES FOR THE PRODUCTION OF FEXOFENADINE

(75) Inventors: Federico Junquera Milla, Zaragoza (ES); William Paul Jackson, Twickenham (GB)

(73) Assignee: Texcontor Establissement, Vaduz (LI)

( * ) Notice: Subject to any disclaimer, the term of this patent is extended or adjusted under 35 U.S.C. 154(b) by 210 days.

(21) Appl. No.: 10/333,974

(22) PCT Filed: Jul. 19, 2001

(86) PCT No.: PCT/IB01/01294

§ 371 (c)(1),
(2), (4) Date: Mar. 19, 2003

(87) PCT Pub. No.: WO02/10115

PCT Pub. Date: Feb. 7, 2002

(65) Prior Publication Data

US 2003/0166682 A1   Sep. 4, 2003

(30) Foreign Application Priority Data

Jul. 28, 2000   (GB) ................... 0018691.6

(51) Int. Cl.
 *C07D 211/223* (2006.01)
(52) U.S. Cl. ..................... 546/240; 546/239
(58) Field of Classification Search ............... 546/240, 546/239
See application file for complete search history.

(56) References Cited

U.S. PATENT DOCUMENTS 5,750,703 A * 5/1998 D'Ambra .................... 546/240
6,242,606 B1 * 6/2001 Krauss et al. ............... 546/239

FOREIGN PATENT DOCUMENTS

EP   0 648 759 A   4/1995
WO   WO 99/47693 A   9/1999

OTHER PUBLICATIONS

Kawai et al. "F facile synthesis . . . " J. Org. Chem. 59, 2620-2622 (1994).*
Kawai et al. "A facile synghesis . . . " CA 120:270048 (1994).*
Morrison and Boyd "Organic chemistry" p. 520 (1973).*
Search result attached.*
Greene "Protectiv groups in organic synthesis" Wiley intersicence p. 10-12 (1982).*
Yodogawa et al. "alpha-(p-butylphenyl)ethyl halides" CA 97:162551 (1982).*
Bymaster et al. "Synthesis of 2,6-dimethyl-1,2,3,4-tetrahydronaphrhalene" CA 106:32509 (1986).*
Gharpure et al. "Synthesis of ar-turmerone employing . . . " CA 107:198677 (1986).*
Kawai et al., "A Facile Synthesis of an Oxidant Product of Terfenadine," *Journal of Organic Chemistry*, 1994, pp. 2620-2622, vol. 59, American Chemical Society, Easton, US.

* cited by examiner

*Primary Examiner*—Celia Chang
(74) *Attorney, Agent, or Firm*—Foley & Lardner LLP

(57) ABSTRACT

An improved process for the manufacture of fexofenadine is described in which a compound of formula (F): wherein $R_2$ represents COOH, COO—$C_{1-6}$ alkyl or CN; and $R_3$ represents hydrogen, mesylate, triflate, tosylate or carboxy-$C_{1-6}$-alkyl, or a salt thereof is prepared by: (I) reacting a compound of formula (B): wherein R1 represents hydrogen or carboxy-$C_{1-6}$-alkyl; and $R_2$ is a hereinbefore defined, with a copper and/or silver compound in the presence of palladium or a compound thereof to yield a compound of formula (C): wherein $R_1$, and $R_2$ are as hereinbefore defined; (II) converting said compound of formula (C) into a compound of formula (E): wherein $R_2$ and $R_3$ are as hereinbefore defined and $R_4$ represents a halogen atom, and (III) reacting said compound of formula (E) with azacyclonol.

3 Claims, 1 Drawing Sheet

PROCESSES FOR THE PRODUCTION OF FEXOFENADINE

BRIEF DESCRIPTION OF DRAWING

FIG. 1 shows a technique for preparing a compound of formula (c) wherein R1 represents CN, as described in J. Med. Chem., 1973, p. 487 and U.S. Pat. No. 3,839,431

Figure 1:
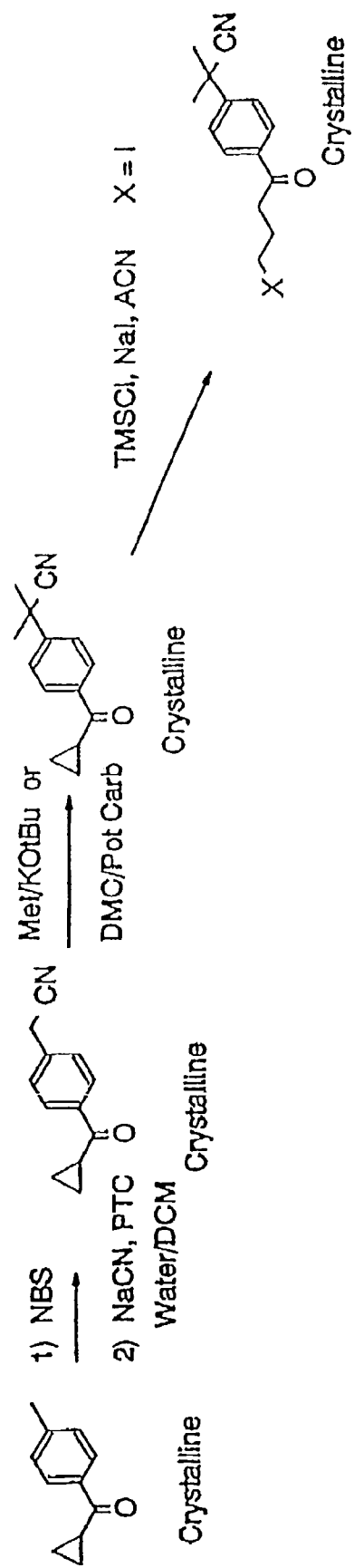
FIG. 1.

This application relates to new processes for the production of fexofenadine and derivatives thereof.

Terfenadine, 1-(p-tert-butylphenyl)-4-[4'-(alpha-hydroxy-diphenylmethyl)-1'-piperidenyl]-butanol, is a non-sedating anti-histamine. It is known to be a specific $H_2$-receptor antagonist that is also devoid of any anticholingeric, antiserotoninergic and antiadrenergic effects both in vivo and in vitro.

However, terfenadine has been linked to potentially fatal abnormal heart rhythms in some patients with liver disease or who also take the antifungal drug ketoconazole or the antibiotic erythromycin In animal and human metabolic studies, terfenadine was shown to undergo high first-pass effect, which results in readily measurable plasma concentrations of the major metabolite 4-[4 [4-(hydroxy diphenyl methyl)-1-piperidenyl]-1-hydroxy butyl]-α,α-dimethylphenyl acetic acid, also known as terfenadine carboxylic acid metabolite or fexofenadine. Fexofenadine possesses anti-histamine activity in animal models and is believed to lack the cardiac side effects seen with terfenadine. Moreover, it has been postulated that terfenadine is in fact a pro-drug and fexofenadine is the active agent.

There has therefore been considerable interest in preparing fexofenadine since its use this may eliminate a number of the side effects associated with the use of terfenadine.

Various synthetic routes to fexofenadine have been proposed in the literature. In *J. Org Chem* 1994, 59, 2620–2622, (Kawai et al) a route is proposed which requires attachment of a four carbon chain to a phenyl acetic acid moiety followed by coupling with the requisite piperidine ring. The method involves the palladium catalysed coupling of a terminal alkyne and aromatic bromide followed by regioselective hydration using environmentally unfriendly mercury after piperidine coupling.

In a series of US Patents, D'Ambra proposes routes to fexofenadine. For example, in U.S. Pat. No. 5,750,703 a process is proposed which involves the reaction of azacyclonol (4- (Ph₂(OH)C)-piperidine) with a cyclopropyl ketone derivative of general formula (I) as illustrated below:

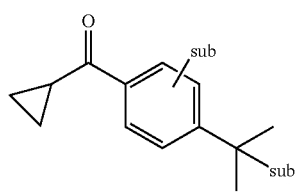

(I)

(wherein sub represents a substituent)

The process is, however, severely limited by the need to provide a substantially pure cyclopropyl regioisomer for reacting with azacyclonol. The cyclopropyl ketone derivative is prepared by the acylation of, for example, an aromatic ester derivative with an acid chloride in the presence of a Lewis acid catalyst. The resulting benzyl derivative comprises a mixture of ortho and para isomers. After formation of a mixture of cyclopropyl ketone isomers, the desired para isomer is isolated labouriously via recrystallisation in low yield.

There still remains the need to provide alternative methods for synthesising fexofenadine and derivatives thereof which overcome the limitations of the prior art processes, e.g. in avoiding the use of hazardous chemicals and the need for labourious and time consuming regioisomer separation techniques.

The applicant has surprisingly found new processes for preparing fexofenadine and derivatives thereof which offer high yielding, stereospecific routes to the desired products without the use of hazardous chemicals and without the need to separate mixtures of isomers. Moreover, it is believed that the processes described below enable fexofenadine to be synthesised much more quickly compared to processes described in the literature.

Thus, viewed from one aspect the invention provides a process for the preparation of a compound of formula (C)

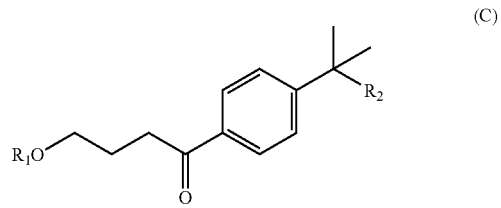

(C)

(wherein $R_1$ represents hydrogen or carboxy-$C_{1-6}$-alkyl; and
$R_2$ represents COOH, COO—$C_{1-6}$-alkyl or CN) or salt thereof comprising reacting a compound of formula (B)

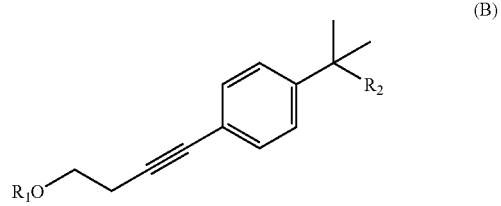

(B)

(wherein $R_1$, and $R_2$ are as hereinbefore defined) with a copper and/or silver compound in the presence of palladium or a compound thereof.

Compounds of formula (C) may then be converted to fexofenadine or derivatives thereof by any convenient route, for example as described in detail below. Fexofenadine may be represented by the formula

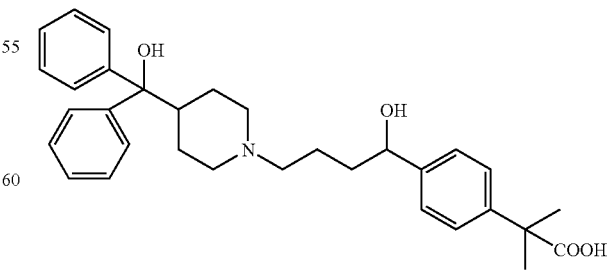

The term "derivatives thereof" is intended to encompass at least salts and esters of the fexofenadine.

In the reaction from compounds (B) to (C), surprisingly, it is believed that the presence of palladium in the reaction mixture accelerates the copper/silver catalysed hydration procedure to allow the reaction to complete, e.g. in 1 to 5 hours, e.g. 2–3 hours. In the absence of palladium it has been found that the same reaction may take 2 days and hence the present invention allows the preparation of compounds of formula (C) rapidly and without the use of toxic and environmentally unfriendly mercury (II) salts. Moreover, the reaction from compound (B) to (C) as claimed herein is one which is suitable for industrial scale.

$R_1$, is preferably hydrogen. $R_2$ is preferably $COOCH_3$, $COOCH_2CH_3$ or CN. When $R_2$ is CN the resulting products are crystalline allowing simple separation and purification.

The copper compound may be any compound capable of catalysing the hydration of a compound of formula (B) and is preferably in its 2+ oxidation state. The copper ions work most efficiently in a non-coordinating anionic environment and may be employed in solution or alternatively bound to a suitable resin. Suitable copper derivatives include copper fluoroborate, copper halides, e.g. copper chloride, copper nitrate, copper sulphate, copper trifluoromethane sulphonate (copper triflate) or Nafion®/copper resin.

The silver compound may also be any compound capable of catalysing the hydration of a compound of formula (B) and is preferably employed in its 1+ oxidation state. The silver ions work most efficiently in a non-coordinating anionic environment and may be employed in solution or alternatively in ion exchange resins. Suitable silver derivatives include silver trifluoromethane sulphonate (silver triflate), silver fluoroborate, silver-hexafluorophosphate and silver nitrate. Silver nitrate is especially preferred since the hydration reaction occurs rapidly and with the production of very minor quantities of unwanted side products.

The palladium compound may be any species capable of accelerating the reaction hereinbefore described. Preferably, the palladium species may be derived from the reactants employed in the preparation of the compound of formula (B). In this regard tetrakis (triphenylphosphine)palladium(0) and derived organic complexes, e.g. bistriphenylphosphine palladium dichloride and bis(benzonitrile) palladium dichloride, are preferred.

The reaction from compound (B) to (C) is conveniently carried out in any suitable solvent, e.g. an alcohol, preferably methanol or especially ethanol. The copper or silver species may be introduced as an aqueous solution. The reaction may be carried out at elevated temperature, e.g. at least 30° C., preferably at least 50° C., especially at reflux. Alternatively the copper and/or silver compound may form part of an ion exchange resin where the reaction may take place using standard techniques associated with the use of ion exchange resins.

The mole ratio of compound of formula (B) to copper and/or silver compound may be between 2:1 to 10:1, more preferably it is about 5:1.

Whilst the majority of the produced compound of formula (C) exists in its open chain format, it is believed that a minor proportion of the product reversibly forms the lactol.

The compounds of formula (B) may be prepared using methods described in the literature. For example, where $R_1$ is hydrogen and $R_2$ represents $COOCH_3$, reference is made to *J. Org Chem* 1994, 59, 2620–2622, (Kawai et al) where chemistry as illustrated in Scheme (1) below is described.

Scheme 1

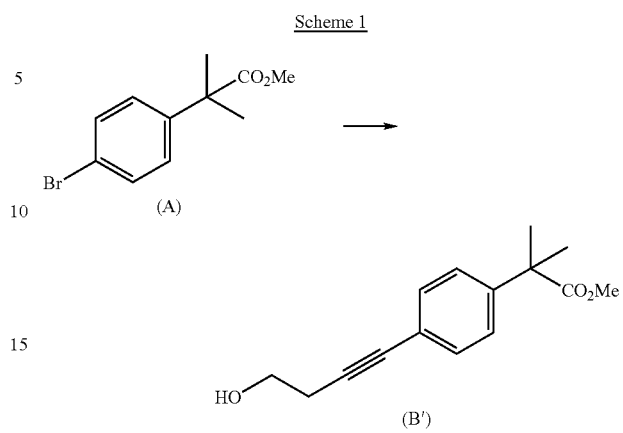

The present inventors have surprisingly found that residual palladium used in the reaction of formula (A) to (B') helps accelerate the formation of compound (C) in the presence of copper and/or silver.

Thus, a labourious isolation of compound (B) is no longer required and the crude compound (B) can be successfully employed. The eventual synthesis of fexofenadine or its derivatives is thus not only simplified but greatly accelerated. Moreover, the hydration of the acetylene is accomplished without the use of the hazardous and environmentally unfriendly mercury compound used by Kawai et al.

Where $R_2$ represents CN the compound of formula (A')

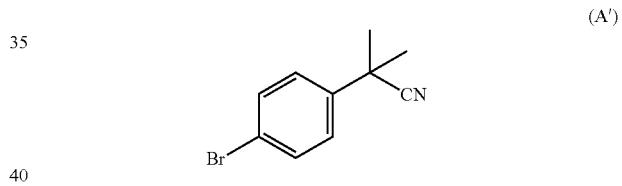

may be readily prepared using the procedure described in EP-A-0163551. This may be converted into a compound of formula (B) using the chemistry described in *J. Org Chem* 1994, 59, 2620–2622, (Kawai et al) discussed above.

The compound of formula (C) may be converted to fexofenadine or a derivative thereof, e.g. salt or ester thereof, by any convenient process. For example, conversion may be accomplished using the chemistry described in U.S. Pat. No. 5,750,703. However, the applicant has devised an improved process for the conversion of a compound of formula (C) to fexofenadine and this forms another aspect of the invention.

It has now been surprisingly found that excellent yields of fexofenadine or derivatives thereof may be obtained if, after conversion of the $R_1O$ group in a compound of formula (C) to a halogen group, the ketone functionality is converted to an alcohol or ester before coupling with the azacyclonol. It is been found that direct reaction of the azacyclonol and bromoketone derivative may be problematic since the azacyclonol may act as a base catalysing the formation of a cyclopropyl ketone derivative. This results in a lowering of yield of product and azacyclonol hydrochloride is formed as a by product. This by product is difficult to remove from the desired product and results in a further lowering of yield during fexofenadine purification.

Thus, viewed from another aspect the invention provides a process for the preparation of a compound of formula (F)

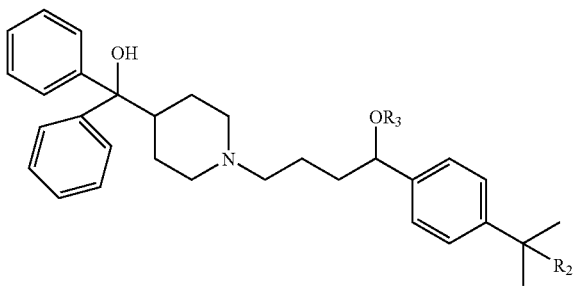

(wherein $R_2$ is as hereinbefore defined and $R_3$ represents hydrogen, mesylate, triflate, tosylate or carboxy-$C_{1-6}$-alkyl) comprising reacting a compound of formula (E)

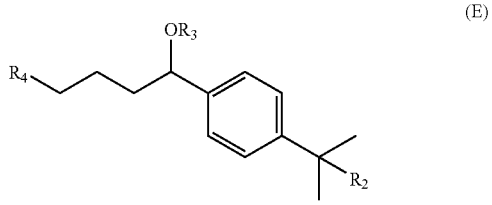

(wherein $R_2$ and $R_3$ are as hereinbefore defined and $R_4$ represents a halogen atom)

with azacyclonol.

As used herein azacyclonol is α,α-diphenyl-4-piperidinemethanol.

Preferences for $R_2$ are as defined above. $R_3$ is preferably carboxyalkyl, especially carboxymethyl, i.e. forming a side chain acetate group. $R_4$ is preferably chloro or bromo.

Using this reaction, it is believed that conversion through to fexofenadine or a derivative thereof may be achieved in excellent yield, e.g. at least 50%, preferably at least 60%, especially at least 80%.

The reaction may be carried out in any suitable solvent, e.g. butanone, optionally in the presence of a weak acid such as a carbonate or iodide ions. The reaction is conveniently heated to reflux.

The compound of formula (E) may be prepared from a compound of formula (C) by standard techniques, e.g. the $R_1O$ functionality may be converted, if necessary, to OH and this may be converted to a halogen using aqueous hydrohalic acid solution. The ketone may be selectively reduced using sodium borohydride and if necessary subsequently esterified.

The compound of formula (E) may of course be prepared by any other suitable process, e.g. by conversion from a compound of formula (G)

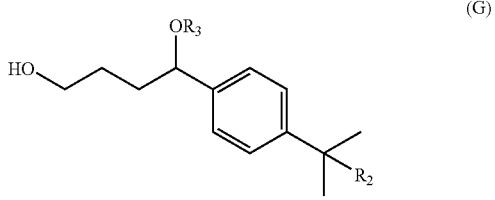

(where $R_2$ and $R_3$ are as herein before defined).

This compound along with compounds of formula (E) and (F) form yet another aspect of the invention.

In another embodiment, a compound of formula (C) wherein $R_2$ represents CN may be prepared by techniques discussed in *J. Med. Chem.*, 1973, p487 and U.S. Pat. No. 3,839,431 and illustrated in FIG. 1. The compound of formula (C) wherein $R_2$ represents CN may be converted to a compound of formula (E) by techniques previously described. This has the advantage over the D'Ambra process described in U.S. Pat. No. 5,750,703 in that no separation of isomers is required, the para-isomer being obtained regiospecifically. Moreover all of the intermediates in the synthesis are crystalline and hence easily purified as required.

Alternatively, where $R_2$ represents CN, a compound of formula (C) may be converted to a compound of formula (D)

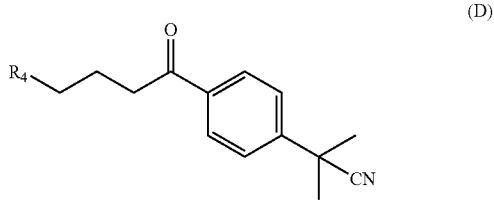

(wherein $R_4$ are as hereinbefore described)

by techniques described above. This compound may be reacted directly with azacyclonol to form a compound of formula (H)

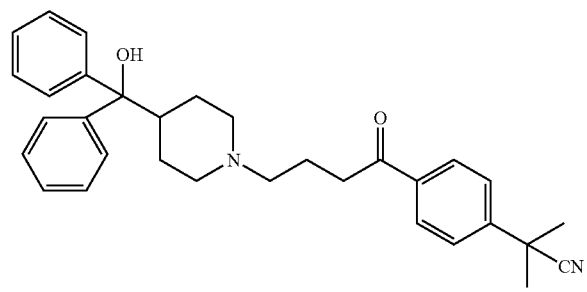

which may be converted to fexofenadine or a derivative thereof by reduction of the ketone and hydrolysis of the nitrile functionality. This process forms yet another aspect of the invention and is especially useful since the key intermediates are again crystalline allowing simple purification, especially from any unwanted cyclopropyl or azacyclonol hydrochloride impurities This is in contrast to derivatives in which the $R_2$ group is an ester which in general are not crystalline.

Moreover, when $R_4$ in a compound of formula (D) is iodo it has been found that less cyclopropyl ketone product is formed, possibly due to the bulk of the iodine atom, and hence yield of fexofenadine is improved.

Conversion of the compound of formula (F) to fexofenadine or a derivative thereof is carried out readily depending on the nature of the $R_{2/3}$ group.

In order to prepare fexofenadine from a compound of formula (F), the $R_3$ group must first, if necessary, be removed by hydrolysis. Where $R_2$ is COOH, no further change is required, however, where $R_2$ represents COO-alkyl then the ester must simply be hydrolysed and where $R_2$ represents CN, simple acid or base catalysed hydrolysis yields the desired COOH group. Thus, a simple hydrolysis of a compound of formula (F) yields fexofenadine or a derivative thereof in one simple step since hydrolysis of the $R_3$ and $R_2$ esters/nitrile may be carried out simultaneously.

The fexofenadine or derivatives thereof provided by the processes of the invention may be formulated and employed in medical treatment as is well-known in the art. For example, fexofenadine may be employed as an antihistamine, antiallergy agent or bronchodilator and may administered alone or in conjunction with other active agents. Pharmaceutical preparations of fexofenadine or its derivatives may take the form of tablets, capsules, powders, solutions, suspensions or emulsions. This may be prepared using conventional pharmaceutical excipients or carriers.

Fexofenadine or its derivatives may be administered orally, parenterally, or across a mucous membrane. The skilled artisan is aware of other administration methods.

The amount of fexofenadine or its derivatives employed will vary depending on the nature of the patient but will be readily determined by the person skilled in the art.

The invention will now be further described with reference to the following non-limiting examples.

Preparations of Methyl 4-(4-hydroxy-1-oxobutyl)-αα-Dimethylphenylacetate.

(Formula C where $R_1$=H, $R_2$=COOMe)

EXAMPLE 1a 2.46 grams (10 mmole) crude 4-(4-Hydroxy-1-butynyl)-α,α-dimethylbenzeneacetic acid, methyl ester (JOC, 1994, 9, 2620) dissolved in 10 ml ethanol is treated with 2 mmole copper fluoroborate in 1 ml water. After 2 hours at reflux, the reaction is shown to be complete by tlc (1:1 ethyl acetate: hexane) and to comprise mainly of the open chain product.

EXAMPLE 1b 2.46 grams (10 mmole) crude 4-(4-Hydroxy-1-butynyl)-α,α-dimethylbenzeneacetic acid, methyl ester (JOC, 1994, 9, 2620) dissolved in 10 ml ethanol is treated with 2 mmole copper trifluoromethane sulphonate in 1 ml water. After 2 hours at reflux, the reaction is shown to be complete by tlc (1:1 ethyl acetate: hexane) and to comprise mainly of the open chain product.

The blank reaction where no copper salt is added shows only traces of the hydrated product.

EXAMPLE 1c

Example 1a was repeated except that highly purified 4-(4-Hydroxy-1-butynyl) -α,α-dimethylbenzeneacetic acid, methyl ester was used in which the Pd residues were removed. In this case, the reaction took about 36 h to be completed.

EXAMPLE 1d 1 gram of crude 4-(4-Hydroxy-1-butynyl)-α,α-dimethylbenzeneacetic acid, methyl ester (JOC, 1994, 9, 2620) was heated with 0.25 equivalents of copper chloride dissolved in 0.5 ml of water and 2.5 ml of industrial methylated spirits. Reaction was complete in 3 hours.

EXAMPLE 1e 1 gram of crude 4-(4-Hydroxy-1-butynyl)-α,α-dimethylbenzeneacetic acid, methyl ester (JOC, 1994, 9, 2620) was heated with 0.25 equivalents of copper nitrate dissolved in 0.5 ml of water and 2.5 ml of industrial methylated spirits. Reaction was complete in 4 hours.

EXAMPLE 1f 1 gram of crude 4-(4-Hydtoxy-1-butynyl)-α,α-dimethylbenzeneacetic acid, methyl ester (JOC, 1994, 9, 2620) was heated with 0.25 equivalents of silver nitrate dissolved in 0.5 ml of water and 2.5 ml of industrial methylated spirites. Reaction was complete in 1 hour with no impurities.

The product gradually cyclises to the lactol at rates depending upon the extraction solvent.

EXAMPLE 2

Large Scale Preparation of Methyl 4-(4-hydroxy-1-oxobutyl)-α,α-dimethylphenylaetate.

Crude methyl 4-(4-Hydroxy-1-butynyl)-α,α-dimethylbenzeneacetic acid (46.7 g, 0.19 mole) is dissolved in 210 ml methanol and diluted with 23 ml water. The mixture was washed with 233 ml hexane then 117 ml hexane, filtering any solids that may have precipitated. The combined hexane fractions are re-extracted with a mixture of 105 ml methanol and 12 ml water. The combined aqueous methanol fractions are treated with copper fluoroborate solution (21.7 ml, 1.75M, 0.038 mole) at reflux for 12 h (complete by tlc). The cooled mixture is filtered through Celite to remove dark particles and the methanol is removed under reduced pressure. The product is dissolved in 233 ml dichloromethane, separated and washed with 233 ml water. After separation, the volume of dichloromethane is reduced by 50% and the solution is used in Example 3.

EXAMPLE 3

Preparation of Methyl 4-(4-bromo-1-oxobutyl)-αα-dimethylphenylacetate.

The dichloromethane solution obtained in Example 2 is stirred with 48% aqueous HBr solution (64.5 ml, 0.57 mole, 3 eq) for 2 h. Tlc (dichloromethane (DCM)) shows the reaction to be complete. The mixture is diluted with 125 ml DCM and 125 ml water. The DCM layer is separated and washed with 50 ml saturated sodium bicarbonate solution and dried over magnesium sulphate. The drying agent is removed and- solvent evaporated to give 45.4 g of a dark oil (71% over 3 stages).

EXAMPLE 4

Preparation of Methyl 4-(4-bromo-1-hydroxybutyl)-αα-dimethylphenylacetate.

(Formula E where $R_4$=Br $R_2$=COOCH$_3$, $R_3$=H)

3.9 g Sodium borohydride is dissolved in 225 ml of methanol that has been pre-cooled to −10° C. 45 g of the Stage 3 ketone, dissolved in 90 ml THF, is added dropwise so that the internal temperature is maintained below 5° C. After about 70% of the ketone solution has been added a further charge of 2.6 g sodium borohydride is added and the addition continued. After a total of 2 h, 125 ml 2M HCl is added and the solvents removed under reduced pressure. The product is extracted with 225 ml DCM, separated and washed with 90 ml saturated sodium bicarbonate solution and dried over magnesium sulphate. The solution is used directly in Example 5.

EXAMPLE 5

Preparation of Methyl 4-(1-acetoxybutyl-4-bromo)-α,α-dimethylphenylacetate.

(Formula E where $R_4$=Br $R_2$=COOCH$_3$, $R_3$=COCH$_3$)
The solution of Example 4 is cooled to about 0° C. and pyridine (22.2 ml, 2 eq) and dimethylaminopyridine (DMAP)
(0.2 g) are added. Acetyl chloride (10.8 ml, 1.1 eq) in 45 ml DCM is added in about 45 min so that the temperature is maintained at 0° C. After 1 h more, 2 M HCl is added (158 ml), the DCM layer separated and then washed with a further 158 ml 2M HCl. The DCM layer is washed with 158 ml saturated sodium bicarbonate solution followed by 158 ml water. After drying, the solvent is removed to give 54 g product (theory 51 g).

EXAMPLE 6

Preparation of Methyl 4-[4-[4-(hydroxydiphenylmethyl)-1-piperidinyl]-1-acetoxybutyl]-α,α-dimethylphenylaceate.

(Formula F where $R_2$=COOCH$_3$, $R_3$=COCH$_3$)
Crude Example 5 product (15.2 g), azacyclonol (10.4 g), potassium bicarbonate (20.5 g), and sodium iodide (1.23 g) are heated at reflux in butanone (152 ml) for 3 h. The cooled reaction mixture is filtered and the solids washed with butanone (45 ml). The solvent is removed, the residual gum dissolved in DCM (76 ml) and washed with water (76 ml). After drying the solvent is removed to give 21.8 g crude product.

EXAMPLE 7

Preparation of 4-[4-[4-(hydroxydiphenylmethyl)-1-piperidinyl]-1-hydroxybutyl]-α,α-dimethylphenyacete acid (fexofenadine).

10.9 g of crude Example 6 product is heated at reflux with 7.8 ml 10M NaOH, 17.6 ml water and 55 ml methanol for 3.5 h. After cooling, the mixture is taken to pH 5 with acetic acid and diluted with 30 ml water. The precipitated solid is cooled for 1 h, filtered, washed with water and dried in vacuum. The solid is then heated with 60 ml DCM and then diluted with 30 ml hexane. The solid is filtered and the process repeated. The solid is dried in vacuum and then heated at reflux with 55 ml methanol. The mixture is cooled in ice/salt, filtered, and washed with 16 ml ice cold methanol. The solid is dried in vacuum at 55–60° C. to give 5.8 g product.

EXAMPLE 8

Preparation of 4-(cyclopropylcarbonyl)-α,α-dimethylphenylacetonitrile 4-(Cyclopropylcarbonyl)phenylacetonitrile, 15.5 g [JOC, 1973,16, 487] and methyl iodide, 15.5 ml, are dissolved in 75 ml THF. The mixture is cooled to −10° C. and a solution of potassium butoxide (24.5 g) in THF (75 ml) is added so that the temperature of the reaction is kept below 5° C. After 0.5 h more, HPLC shows the reaction to be complete. 200 ml 2M HCl is added followed by 200 ml toluene. The organics are washed with 100 ml 10%. sodium sulphite solution then 100 ml satd sodium chloride solution. The THF is removed and the toluene treated with 5 g silica to remove colour. The toluene is removed and the product crystallises. Yield, 19 g.

EXAMPLE 9

Preparation of 4-(4-iodo-1-oxobutyl)-α,α-dimethylphenylacetonitrile

Example 8 product, 7.9 g and sodium iodide, 8.05 g are mixed in acetonitrile (55 ml). Trimethylsilyl chloride (7 ml) is added in a single portion and the mixture stirred for 1 h. The solvent is removed under reduced pressure and toluene (100 ml) and water (50 ml) is added. The aqueous layer is separated and the toluene solution washed with 50 ml 10% sodium sulphite solution then 50 ml water. The solvent is removed and the product crystallises on standing, 12.7 g.

EXAMPLE 10

Preparation of 4-[4-[4-(hydroxydiphenylmethyl)-1-piperidinyl]-1-oxobutyl]-α,α-dimethylphenylacetonitrile Example 9 product, 38 g, is dissolved in 170 ml toluene and added during 1 h to a mixture of azacyclonol (59 g) and potassium carbonate (45.6 g) in toluene (340 ml) at 100° C. After 2 more hours, the mixture is cooled, filtered and the solvent removed. The resulting solid is slurried in 140 ml ethyl acetate and 140 ml hexane added. After 1 h at 5° C., the solid is filtered and washed with 40 ml 1:1 ethylacetate:hexane.

Product weight, 46.5 g. HPLC shows about 12% residual azacyclonol as the iodide salt.

EXAMPLE 11

Preparation of 4-[4-(4-hydroxydiphenylmethyl)-1-piperidinyl]-1-hydroxybutyl]-α,α-dimethylphenylacetic acid (fexofenadine)

Example 10 product, 36 g, is added to 300 ml IMS and heated to 60° C. 24 g of a 12% solution of sodium borohydride in 40% aqueous caustic is added. A complete solution is obtained, but the mixture solidifies after about 5 mins. 75 g potassium hydroxide and 15 ml water are added and the mixture heated to reflux for 24 h. After cooling, 200 ml water is added and the mixture is acidified to pH 5 with about 75 ml acetic acid. About 150 ml ethanol is removed and 300 ml water is added. After 0.5 h the solids are filtered and washed with 2×200 ml water. The solid is air-dried as much as possible before being heated in 250 ml methanol for 2 h. Cool to 0° C. for 1 h and filter. Wash with 50 ml cold methanol and dry at 55° C. under vacuum. Yield, 29.3 g. HPLC purity >99.8% AUC.

EXAMPLE 12

Preparation of 4-(4-hydroxy-1-butynyl)-α,α-dimethylphenylacetonitrile (Formula B where $R_1$=H $R_2$=CN)
2-(4-Bromophenyl)-2,2-dimethylacetonitrile (Eu Pat, 0163551, 1985), 22.4 g, butynol, 10.5 g, triethylamine, 21 ml, and ethyl acetate, 62.5 ml are vigorously heated under nitrogen for 1 h to de-gas. The mixture is cooled to below reflux and a mixture of copper (I) iodide, 0.495 g and bis-triphenylphosphine palladium dichloride, 0.77 g are added. The mixture is then heated at reflux for a further 4 h. The mixture is cooled to room temperature and diluted with 100 ml toluene. The mixture is washed with 2M HCl (2×150 ml) and then water (150 ml). The organics are removed to about half volume to remove the ethyl acetate and the toluene solution is treated with 5 g silica. The solution is filtered and evaporated to give 21.4 g of an orange oil.

The oil is dissolved in methanol (96 ml), diluted with water (10.7 ml) and washed with hexane (107 ml then 54 ml). The combined hexane washings are extracted with 54 ml 9:1 methanol:water. The combined methanol fractions are evaporated, diluted with 150 ml toluene and dried. After removal of solvent, the remaining oil solidifies, 20.2 g.

A portion (5 g) is crystallised from toluene:hexane to recover 3.9 g, mpt 72-75° C.

EXAMPLE 13

Preparation of 4-(4-hydroxy-1-oxobutyl)-α,α-dimethylphenylacetonitrile (Formula C where $R_1$=H $R_2$=CN)

Crude Example 12 product (6.4 g) is dissolved in IMS (33 ml) and 1.75 M copper fluoroborate solution is added (3.3 ml). The mixture is heated at reflux for 10 h. The solvent is removed and DCM (50 ml) and water (25 ml) are added. The DCM layer is washed with water (25 ml) and then filtered through celite. After removal of the solvent, 7.22 g crude product is obtained (theory 6.94 g).

EXAMPLE 14

Preparation of 4-(4-bromo-1-oxobutyl)-α,α-dimethylphenylacetonitrile

The crude Example 13 product is dissolved in DCM (14 ml) and stirred with aqueous 48% HBr solution (10.2 ml) for 2 h. The mixture is diluted with 25 ml DCM and 50 ml water. The DCM layer is separated and washed with water until the washings are neutral. The DCM solution is dried and then filtered through a short pad of silica washing with further DCM to collect the product. The product containing fractions are combined and the solvent removed to give 5.26 g of an orange solid, which crystallises on standing.

What is claimed is:

1. A process for the preparation of a compound of formula (F)

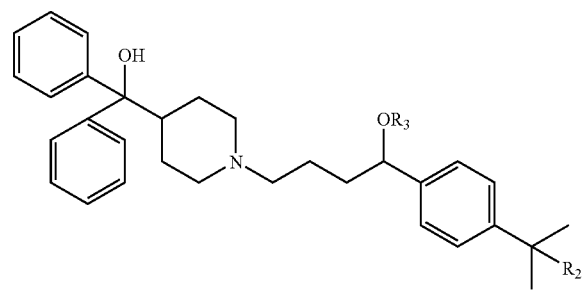

(F)

(wherein $R_2$ represents COOH or COO-$C_{1-6}$ alkyl; and $R_3$ represents hydrogen, mesylate, triflate, tosylate or carboxy-$C_{1-6}$-alkyl) or a salt thereof comprising:

(I) reacting a compound of formula (B)

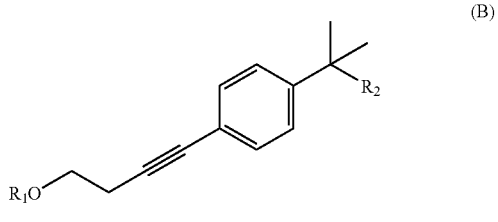

(B)

(wherein $R_1$ represents hydrogen; and
$R_2$ is as hereinbefore defined) or a salt thereof with a copper and/or silver compound in the presence of palladium or a compound thereof to yield a compound of formula (C)

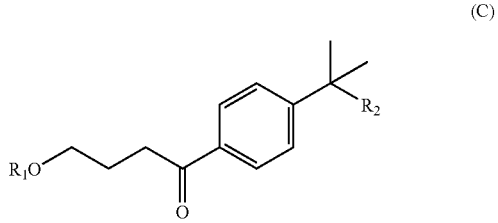

(C)

(wherein $R_1$ and $R_2$ are as hereinbefore defined);

(II) converting said compound of formula (C) into a compound of formula (E)

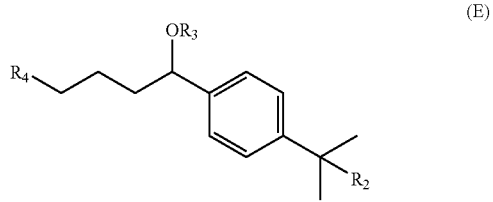

(E)

(wherein $R_2$ and $R_3$ are as hereinbefore defined and $R_4$ represents a halogen atom) or a salt thereof; and (III) reacting said compound of formula (E) with azacyclonol.

2. A process as claimed in claim 1 wherein $R_3$ is carboxy-$C_{1-6}$-alkyl.

3. A process as claimed in claim 1 further comprising converting said compound of formula (F) into fexofenadine or a pharmaceutically acceptable salt thereof.

* * * * *